United States Patent
Wright

(10) Patent No.: US 6,945,953 B2
(45) Date of Patent: Sep. 20, 2005

(54) DISPENSING APPARATUS FOR DELIVERING POWDERED PRODUCT

(75) Inventor: Andrew David Wright, Norfolk (GB)

(73) Assignee: Bespak PLC (GB)

(*) Notice: Subject to any disclaimer, the term of this patent is extended or adjusted under 35 U.S.C. 154(b) by 286 days.

(21) Appl. No.: 10/248,439

(22) Filed: Jan. 21, 2003

(65) Prior Publication Data

US 2003/0178440 A1 Sep. 25, 2003

(30) Foreign Application Priority Data

Jan. 22, 2002 (GB) ............................................ 0201409

(51) Int. Cl.$^7$ .......................................... A61M 13/00
(52) U.S. Cl. ...................................................... 604/58
(58) Field of Search ....................... 604/58, 59, 68–72, 604/86, 89–92

(56) References Cited

U.S. PATENT DOCUMENTS

| 2,307,986 A | 1/1943 | Bolte et al. |
| 2,672,144 A | 3/1954 | Cohen |
| 3,272,442 A | 9/1966 | Rink et al. |
| 4,017,007 A | 4/1977 | Riccio |
| 4,034,899 A | 7/1977 | Meshberg |
| 4,252,848 A | 2/1981 | Datta et al. |

(Continued)

FOREIGN PATENT DOCUMENTS

| DE | 197 00 838 A1 | 7/1998 |
| DE | 199 42 791 A | 3/2001 |
| EP | 0 360 463 | 3/1990 |
| EP | 0407276 A | 1/1991 |
| EP | 0 407 276 A | 1/1991 |
| EP | 0469926 | 2/1992 |
| EP | 0 808 635 A2 | 11/1997 |
| EP | 0 906 765 A1 | 4/1999 |
| FR | 2 775 963 A | 9/1999 |
| GB | 1 338 254 | 11/1973 |
| GB | 2087355 A | 5/1982 |
| GB | 2 367 756 A | 4/2002 |
| WO | WO 9102558 | 3/1991 |
| WO | WO 9106333 | 5/1991 |
| WO | WO 92/06727 | 4/1992 |
| WO | WO 93/11818 A | 6/1993 |
| WO | WO 96 28367 A | 9/1996 |
| WO | WO 9632345 | 10/1996 |
| WO | WO 97 32672 | 9/1997 |
| WO | WO 97 47347 | 12/1997 |
| WO | WO 98/51360 | 11/1998 |
| WO | WO 98/55168 | 12/1998 |
| WO | WO 99/42154 | 8/1999 |
| WO | WO 99 42154 | 9/1999 |
| WO | WO 99/46055 | 9/1999 |
| WO | WO 99 49923 A | 10/1999 |
| WO | WO 00/16835 | 3/2000 |
| WO | WO 2001/010742 A1 | 2/2001 |
| WO | WO 01 43529 A | 6/2001 |
| WO | WO 02 305500 A | 4/2002 |

Primary Examiner—Anhtuan T. Nguyen
(74) Attorney, Agent, or Firm—Morris, Manning & Martin LLP

(57) ABSTRACT

A dispensing device for dispensing a powdered product includes a housing having a first end and a second end defining a first outlet; a plunger slidably received in the first end of the housing, the housing and plunger together defining an interior of the dispensing device which is open to atmosphere; a chamber located within the plunger for housing a powdered product; a sheathing member slidably mounted on an end of the plunger proximate the second end of the housing, and having an inlet and a second outlet closed by a frangible membrane. Additionally, the plunger includes a perforating element for puncturing the frangible membrane when the plunger is moved towards the second end of the housing.

27 Claims, 4 Drawing Sheets

U.S. PATENT DOCUMENTS

| | | |
|---|---|---|
| 4,417,890 A | 11/1983 | Dennehey et al. |
| 4,645,487 A | 2/1987 | Shishov et al. |
| 4,844,986 A | 7/1989 | Karakelle et al. |
| 4,857,080 A | 8/1989 | Baker et al. |
| 4,875,605 A | 10/1989 | Weston |
| 4,948,628 A | 8/1990 | Montgomery et al. |
| 5,341,800 A | 8/1994 | Clark et al. |
| 5,349,944 A | 9/1994 | Chippendale et al. |
| 5,474,758 A | 12/1995 | Kwon |
| 5,490,497 A | 2/1996 | Chippendale et al. |
| 5,576,068 A | 11/1996 | Caburet et al. |
| 5,683,361 A | 11/1997 | Elk et al. |
| 5,775,321 A | 7/1998 | Alband |
| 5,836,299 A | 11/1998 | Kwon |
| 5,857,456 A | 1/1999 | Sun et al. |
| 5,871,010 A | 2/1999 | Datta et al. |
| 5,884,820 A | 3/1999 | Thanisch et al. |
| 5,904,274 A | 5/1999 | Warby et al. |
| 6,006,745 A | 12/1999 | Marecki |
| 6,039,042 A | 3/2000 | Sladek |
| 6,120,481 A | 9/2000 | Rennert et al. |
| 6,131,566 A | 10/2000 | Ashurst et al. |
| 6,253,762 B1 | 7/2001 | Britto |
| 6,358,569 B1 | 3/2002 | Badyal |

PRE-ACTUATION
POSITION
(STORAGE)

ACTUATION
POSITION (DISPENSING)

PRE-ACTUATION
POSITION
(STORAGE)

DISPENSING APPARATUS FOR DELIVERING POWDERED PRODUCT

CROSS REFERENCE TO RELATED APPLICATIONS

The present patent application claims priority under 35 U.S.C. to patent application GB 0201409.0 filed Jan. 22, 2002, which is incorporated herein by reference.

BACKGROUND OF INVENTION

The present invention relates to a disposable dispensing apparatus for delivering a powdered product nasally or orally. More specifically, but not exclusively, there is provided a single use dry powder medicament inhaler which can be used by persons who have not had medical training.

Such dispensing devices are well known in the art and are of particular use for the dispensing of drugs which can easily be absorbed through the nasal or pulmonary passages, especially for drugs which only need to be dispensed occasionally.

A dispensing device is known from U.S. Pat. No. 5,683,361 (incorporated herein by reference) which dispenses a single dosage of a powdery drug which is stored in a cylindrical storage chamber within the sealed main body of the device until dispensation of the drug is required. The chamber is located in an axially displaceable piston, which is mounted in the main body of the device between an end wall of the main body and a plunger for releasing the drug. The chamber is sealed with breakable membranes at either end of the cylinder which are, upon activation of the dispensing device, punctured by one or more perforating elements. An outlet duct is provided at the end of the main body remote from the plunger for dispensation of the drug to the user. The perforating element is provided at the end of the outlet duct nearest to the piston to puncture at least the outermost membrane of the drug chamber.

Both embodiments of the device described in U.S. Pat. No. 5,683,361 involve pressurization of the air inside the device prior to dispensation of the powdered medicament. When the plunger is pressed by the user into the main body of the device a pocket of air, which is trapped inside the main body of the device between the piston and the plunger, is compressed and the pressure inside the device increases. This increase in pressure causes the piston to move towards the outlet duct of the dispensing device, thereby causing the outermost membrane to be punctured by the perforating element. The remaining intact membrane is then punctured in one of two possible ways: by the penetrating element provided at the inner end of the outlet duct as the plunger, and therefore also the piston, is pushed further into the main body of the device, or by a second perforating element which is optionally provided at the inner end of the plunger.

A disadvantage with the devices described in U.S. Pat. No. 5,683,361 is that they do not always dispense the whole drug dose to the patient. As the outermost membrane is punctured, pieces of the perforated membrane are pushed into the chamber in the opposite direction to movement of the plunger and the desired drug flow path. This results in some of the powdered drug particles being trapped between pieces of the perforated membrane and the wall of the chamber as the drug is forced out of the dispensing device via the outlet duct. Furthermore, as the patient inhales, the pieces of the perforated membrane are drawn in the direction of the outlet duct and thereby interfere with the dispensing of the drug as the powder can no longer flow freely out of the drug chamber. In this way, the dose dispensed by the device is often incomplete, which can mean that the drug is not wholly effective.

Another single-use dispensing device is described in patent application GB 0025027.4 (incorporated herein by reference) which device comprises a bellows unit for pressurizing the interior of the device and for propelling the powdered drug out of the dispensing apparatus.

A single-use dispensing device needs to be simple and cheap to manufacture. The known devices described above require a sealed main body to enable the device to be pressurized.

SUMMARY OF INVENTION

According to the present invention there is provided a dispensing device for dispensing a powdered product comprising a housing, having a first end and a second end defining a first outlet, a plunger slidably received in the first end of the housing, the housing and plunger together defining an interior of the dispensing device which is open to atmosphere, a chamber located within said plunger for housing a powdered product, a sheathing member slidably mounted on an end of the plunger proximate the second end of the housing, and having an inlet and a second outlet closed by a frangible membrane, and the plunger comprising a perforating element for puncturing the frangible membrane when the plunger is moved towards the second end of the housing.

DETAILED DESCRIPTION

A preferred embodiment of the present invention will now be described by way of example only and with reference to the accompanying drawings.

Figure 1:
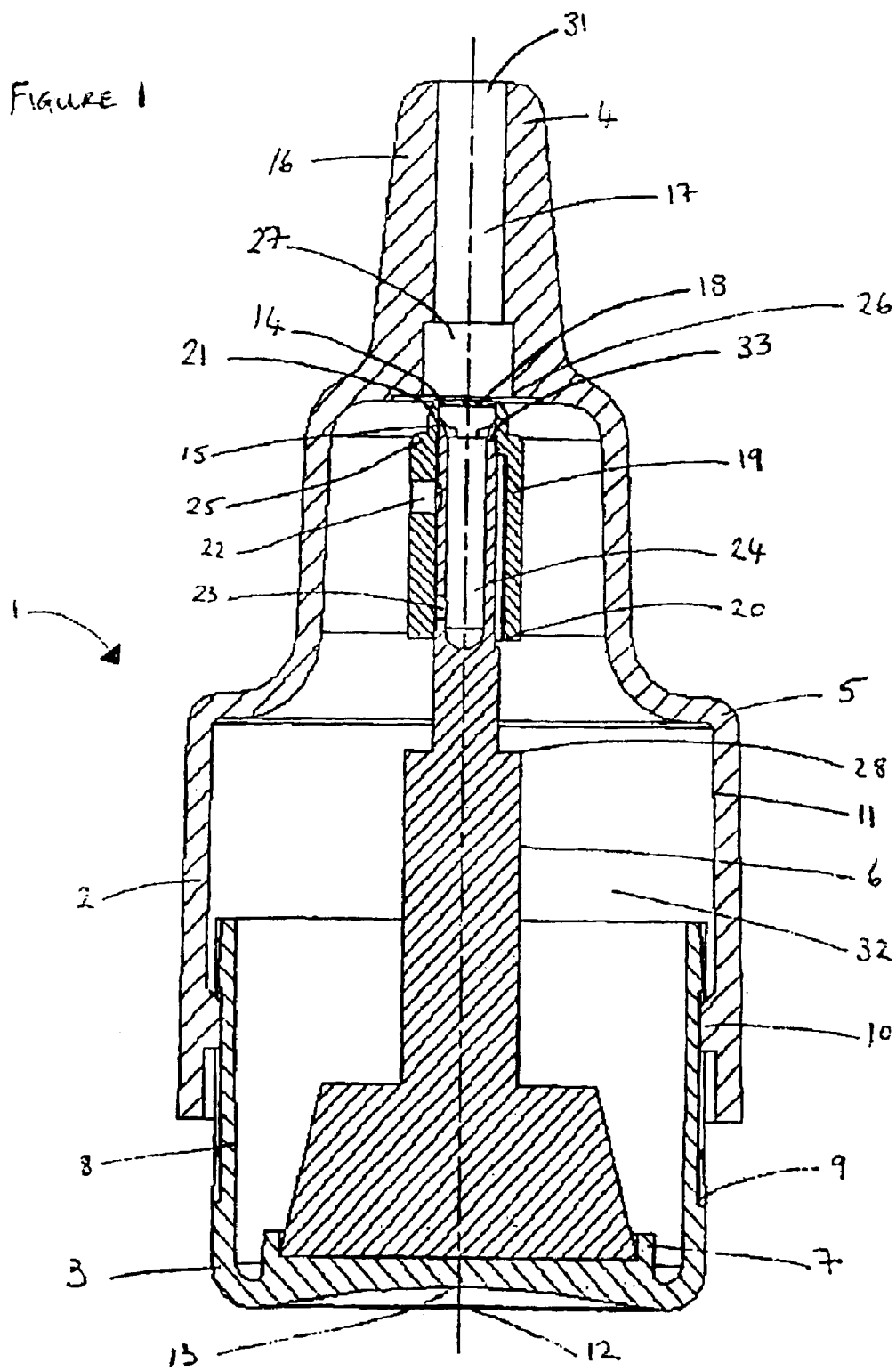
FIG. 1 is a cross-sectional view of a first embodiment of a dispensing apparatus according to the present invention in a storage condition.
Figure 2:
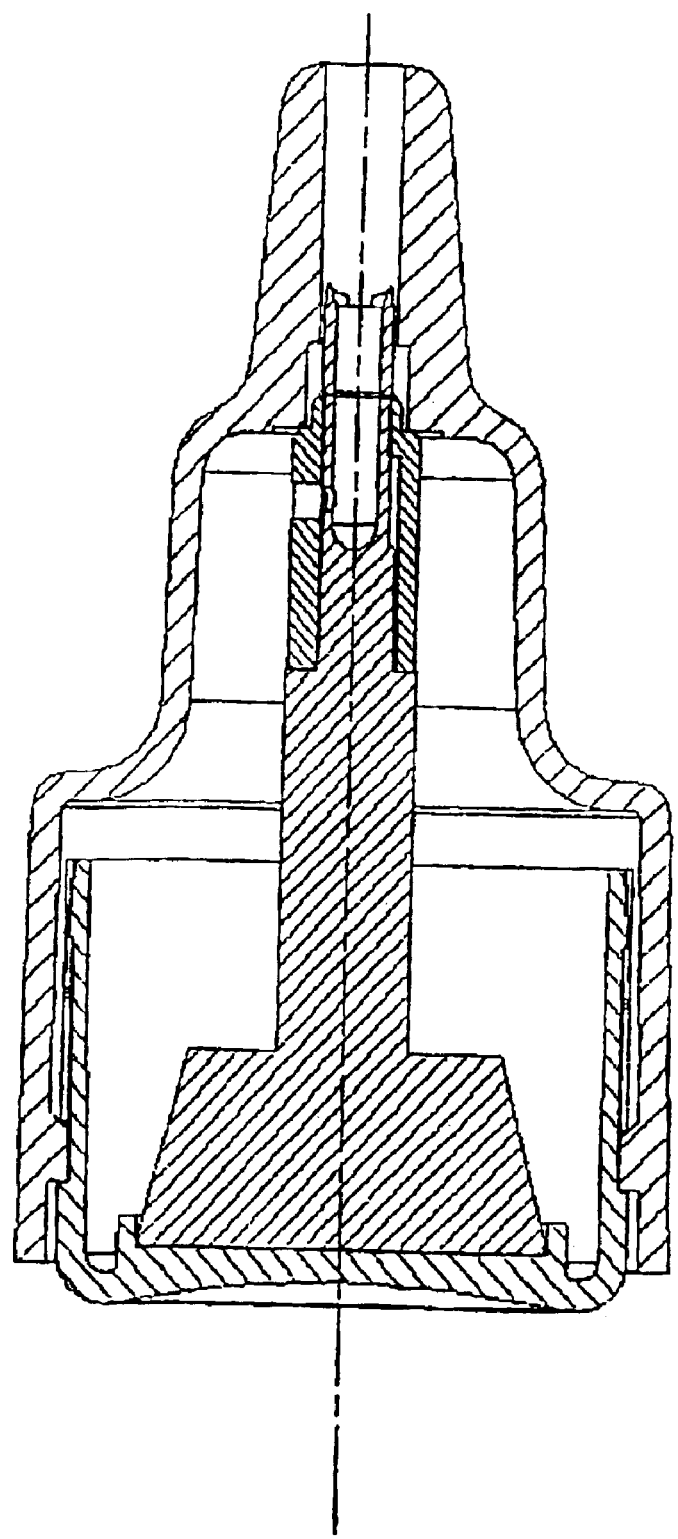
FIG. 2 is a cross-sectional of the apparatus of FIG. 1 in a dispensing condition.

As shown in FIGS. 1 and 2, the apparatus of the present invention comprises a housing 1, a plunger 3 and a sheath 19. The housing 1 comprises a generally tubular body 2 of varying diameter having an open second end forming a first outlet 31 in a tip 4 and an open first end in which the plunger 3 is slidably received. The housing 1 is provided with an external shoulder 5 for use as a finger rest. Alternatively, the housing 1 may be provided with a protruding lip to act as a finger rest.

The tip 4 comprises an outer wall 16 which defines an outlet duct 17 through which medicament may be dispensed. An innermost end of the outlet duct 17 is provided with an enlarged duct 27 which has a larger cross-sectional diameter than the outlet duct 17. The innermost end of the enlarged duct 27 is provided with a shoulder 26.

The tip 4 is frusto-conically shaped so as to form a nozzle which is inserted, in use, into a patient's nostril. However, the tip 4 may also be shaped into a substantially cylindrical shape or similar, suitable for insertion, in use, into a patient's mouth.

The plunger 3 comprises a substantially cylindrical body 8 and a probe 6. The body 8 is closed at one end to form an end face 12. The opposite end is left open. The probe 6 is coupled or joined to an inner surface of the end face 12 and projects there from. The probe 6 is coupled to the end face 12 by means of a retaining lip 7, although in an alternative embodiment the probe 6 and plunger 3 may be moulded as one piece, therefore avoiding the need for a retaining lip 7. With the plunger 3 received in the housing 1, the probe 3 projects towards the first outlet 31 of the tip 4. Together, the plunger 3 and housing 1 define an interior 32 of the apparatus.

The probe 6 is substantially cylindrical in shape and is provided with an inwardly directed shoulder 28. Alternatively, the inwardly directed shoulder 28 could be replaced by a flange. An end 33 of the probe 6 remote from the end face 12 is provided with a piercing tip 14. The piercing tip 14 is provided with a sharpened cutting edge 15.

A portion of the probe 6, at the end 33 of the probe 6, is provided with a hollow bore forming a storage chamber 24. The storage chamber extends upwardly to the piercing tip 14. A radially directed aperture 23 is provided through the thickness of the wall of the probe 6 communicating with a lower end of the storage chamber 24.

The storage chamber 24 is substantially cylindrical in shape and is large enough to contain a single dose of powdered medicament which is to be dispensed. The powdered medicament is located in an end of the storage chamber 24 remote from the tip 4. Likewise, the aperture 23 is located at the end of the storage chamber 24 remote from the tip 4.

An external surface of the body 8 of the plunger 3 is provided with at least one axially oriented channel 9. Each channel 9 receives a lug 10 which is located on an inner surface 11 of the housing 1. The lug 10 and channel 9 arrangement prevents the plunger 3 from being withdrawn fully from the housing 1. The channel 9 also allows for air from atmosphere to pass between the plunger 3 and the housing 1, since the interference fit is not air tight.

The end face 12 of the plunger 3 is provided with an indentation 13 which is suitable for use as a thumb rest.

A sheath 19, which is substantially cylindrical in shape, is slidably received over the end 33 of the probe 6 remote from the end face 12. The sheath 19 comprises an open end 20 for receiving the probe 6 and an opposite closed end 21, which is closed by a frangible membrane 18. An aperture 22 is provided in the sheath 19. The aperture 22 is in the form of a radially directed inlet which passes through the wall thickness of the sheath 19. An outwardly directed shoulder 25 is provided on the sheath 19 in the vicinity of the closed end 21.

Figure 3A:
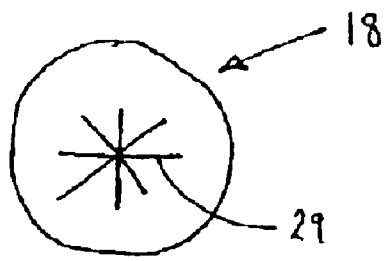
FIGS. 3a, 3b and 3c show plan views of three variants of frangible membranes for use in the dispensing device of the present invention.
Figure 3B:
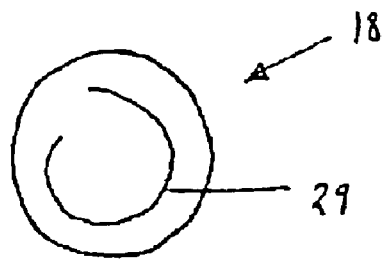
Figure 3C:
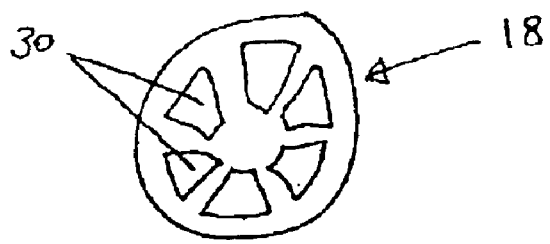

Typically, the thickness of the frangible membrane 18 is between 0.03 and 0.20 mm. Furthermore, as shown in FIGS. 3a and 3b, the membrane 18 is provided with one or more pre-formed lines of weakness 29 to aid the rupturing of the membrane by the piercing tip 14. FIG. 3a depicts a star pattern of weaknesses and FIG. 3b depicts a half-moon pattern of weaknesses. Alternatively, the frangible membrane 18 may comprise a plurality of castellations 30 which are of a reduced thickness compared to the rest of the frangible membrane 18 as shown in FIG. 3c.

In a storage position, as shown in FIG. 1, the sheath 19 is mounted on the probe 6 with the piercing tip 14 in close proximity but not quite abutting against the frangible membrane 18. In this position, the radial apertures 22 and 23 are out of alignment and there is consequently no open flow path between the interior 32 of the housing 1 and the storage chamber 24. Thus, the apertures 22 and 23, which together form an inlet valve are in a closed position. However, there is an open flow path from the interior 32 of the housing 1 to the outlet duct 17, via the duct 27.

In use, a user holds the apparatus typically by means of two or more fingers positioned on the external shoulder 5 and a thumb positioned on the end face 12. The tip 4 is then inserted into the nose (or mouth if the apparatus is for pulmonary use). Inhalation at this stage is possible freely but is ineffective since air is drawn from the interior 32 of the housing 1 through the enlarged duct 27 and out via the outlet duct 17. Pressure in the interior 32 is equalized by air flow into the interior 32 between the plunger 3 and the housing 1.

The user depresses the end face 12 of the plunger 3 relative to the housing 1 so as to move the probe 6 and sheath 19 axially in the direction of the tip 4. Initially, the probe 6 and the sheath 19 are free to move unhindered into the enlarged duct 27.

Further movement of the probe 6 and sheath 19 brings the outwardly directed shoulder 25 of the sheath 19 into contact with the internal shoulder 26 of the enlarged duct 27. At this point, further movement of the sheath 19 towards the tip 4 is prevented. The abutment of the outwardly directed shoulder 25 of the sheath 19 against the internal shoulder 26 also closes the flow path from the interior 32 of the housing 1 to the outlet duct 17. Continued movement of the probe 6 towards the tip 4 causes the probe 6 to slide relative to the sheath 19 and the piercing tip 14 of the probe 6 to pierce and break the frangible membrane 18.

Advantageously, the frangible membrane 18 is ruptured from below with the piercing tip 14 moving relative to the membrane 18 in the direction of tip 4. As a result the flap of the membrane 18 which is left after rupture is positioned above the membrane periphery such that as powdered medicament particles pass the membrane 18 the flap tends to be moved away from the hole formed in the membrane so as not to block the flow path.

Subsequent inward movement of the probe 6 causes the storage chamber 24 to be moved into the outlet duct 17. During this stage of actuation, air within the housing 1 can escape between the plunger 3 and the housing 1. Further relative axial movement of the sheath 19 and probe 6 causes the apertures 22 and 23 to come into alignment, opening the inlet valve of the storage chamber 24. The apparatus is now in the dispensing position, as shown in FIG. 2.

In the dispensing position the inlet valve is open and the frangible membrane 18 is ruptured. Thus a continuous flow path is established between the interior 32 of the housing 1, and the outlet duct 17 via the storage chamber 24. As a result, upon inhalation air is displaced from the interior 32 of the housing 1, through the inlet valve formed by the apertures 22 and 23 and into the storage chamber 24 where it entrains the powdered product. The air and entrained product is then displaced through the piercing tip 14, and outlet duct 17 where it exits the apparatus and is inhaled.

Movement of the probe 6 is finally limited by abutment of the inwardly directed shoulder 28, against the open end 20 of the sheath 19.

Figure 5:
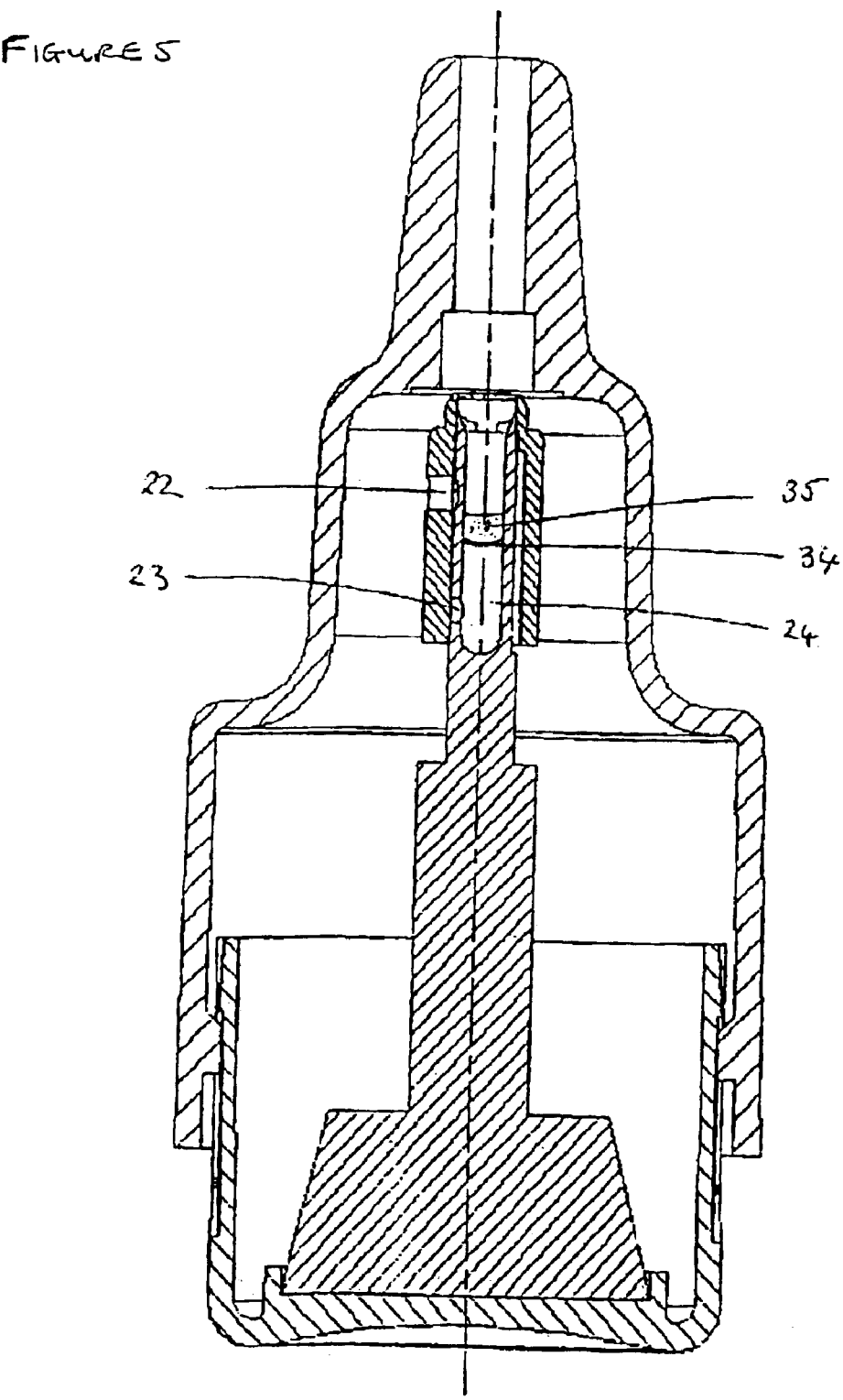
FIG. 5 is a cross-sectional of a second embodiment of a dispensing apparatus according to the present invention in a storage condition.

In an alternative embodiment of the invention, shown in FIG. 5, a second porous membrane 34 is provided in the storage chamber 24, between the aperture 23 and the piercing tip 14, on which a single dose of powdered medicament 35 is located. During use of this alternative embodiment, the tip 4 is placed into the nose or mouth and the end face 12 is depressed relative to the housing 1 so that the apparatus is in a dispensing position. During subsequent inhalation by the user, air is displaced from the interior 32 of the housing 1 through the apertures 22, 23 into the storage chamber 24. Due to the porosity of the second membrane 34, the air travels through the membrane 34, thus entraining the powdered medicament 35 such that air and powdered medicament 35 exit the apparatus via the first outlet 31 and are inhaled. The second membrane 34 may be made of a porous paper, sintered plastic or similar material, provided that the pore size of the material is large enough to allow air through but small enough not to allow the powdered medicament 35 through.

The dispensing device is described above as being placed in the nose, or mouth as the case may be, before the device is actuated. However, the dispensing device may also be actuated prior to insertion of the tip 4 into the nose or mouth, as long as the device is maintained in an upright position to avoid spillage of the powdered medicament prior to insertion of the device in the nose or mouth.

The dispensing apparatus may be provided in a sterile package such as a foil packet in order to prevent moisture from affecting the apparatus, and also for reasons of hygiene. The apparatus will not function adequately if the powdered drug becomes damp. Alternatively, a cover may be provided to encase and close tip 4 before use.

Figure 4:
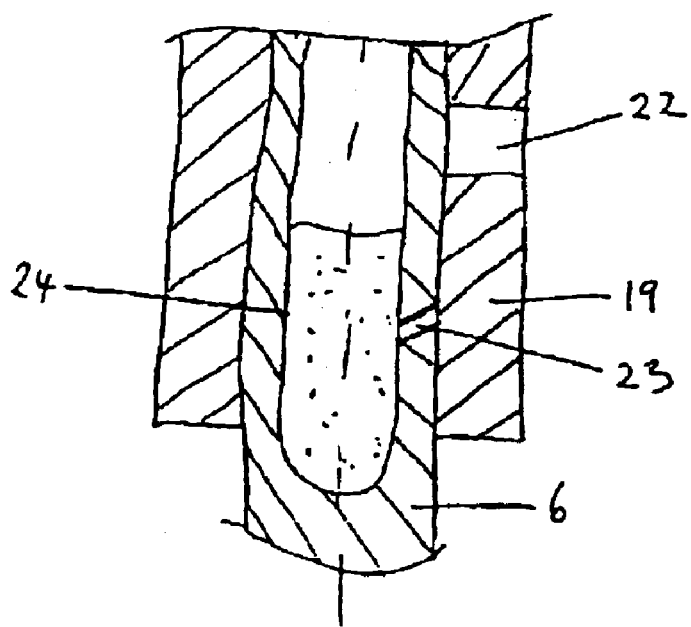
FIG. 4 is a cross-sectional of a part of the dispensing device of the present invention showing a variant storage chamber inlet aperture.

FIG. 4 shows a variant of the aperture 23 wherein the aperture is directed so as to have a component in the axial direction as well as the radial direction. In this way the air entering the storage chamber 24 is directed towards the closed lower end of the chamber 24 so as to more efficiently entrain the powdered product. Alternatively, the inlet aperture 23 may be angled so as to have components in the radial, axial and circumferential directions such that air entering the storage chamber 24 is directed towards the lower end of the chamber 24 with a spiraling motion. In any of these arrangements the inlet aperture 23 may be positioned so as to be covered or uncovered by the powdered product in the storage condition. More than one aperture 23 may be provided.

Alternatively, the inlet aperture 23 may be positioned in the lower end of the storage chamber 24 such that air entering the chamber enters underneath the powdered product and is directed axially along the chamber 24 towards the piercing tip 14. In a yet further alternative, the powdered product may be suspended on a mesh within the storage chamber 24 such that air entering the storage chamber 24 enters below the mesh and entrains the powdered product as it passes through the mesh.

Optionally, the storage chamber 24 may be provided with rifling grooves or similar along its length to impart a spiraling motion to the air and entrained product as it passes along the chamber towards the piercing tip 14.

In the above description, item 19 is described as a "sheath". This item may be in the form of a cap, case or similar.

The housing 1, plunger 3, probe 6 and sheath 19 are manufactured from polyethylene, polypropylene, polyester, any engineering plastic or a similar material. Similarly, the frangible membrane 18 is manufactured from polyethylene or polypropylene or a similar material. Alternatively, the probe 6 may be manufactured from a metal such as stainless steel.

The variants described above may be combined with the described embodiments in any combination as will be obvious to the skilled person.

Advantageously, the materials of the dispensing apparatus lend themselves to easy and ready recycling. In the preferred embodiment, the absence of any metallic or ceramic components reduces the cost of processing the recycled material.

Advantageously, the components of the dispensing apparatus are moulded. This leads to low levels of material waste. The current design allows for a low number of individual parts which reduce the assembly time and cost. In a preferred embodiment of the invention, the whole apparatus may be formed from only three components, the first component being the housing 1 including the tip 4, the second component being the plunger 8 and probe 6 and the third component being the sheath 19 including the frangible membrane 18.

What is claimed is:

1. A dispensing device for dispensing a powdered product comprising:
    a housing, having a first end and a second end defining a first outlet;
    a plunger slidably received in the first end of the housing, the housing and plunger together defining an interior of the dispensing device which is open to atmosphere;
    a chamber located within said plunger for housing a powdered product; and
    a sheathing member slidably mounted on an end of the plunger proximate the second end of the housing, and having an inlet and a second outlet closed by a frangible membrane;
    wherein the plunger comprises a perforating element for puncturing the frangible membrane when the plunger is moved towards the second end of the housing.

2. A dispensing device as claimed in claim 1, wherein the interior of the dispensing device is open to atmosphere by means of a gap between the plunger and the housing.

3. A dispensing device as claimed in claim 1, wherein the interior of the dispensing device is open to atmosphere via the first outlet.

4. A dispensing device as claimed in claim 1, wherein the frangible membrane is between 0.03 and 0.20 mm in thickness.

5. A dispensing device as claimed in claim 1, wherein the frangible membrane comprises one or more castellations to aid rupture of said membrane.

6. A dispensing device as claimed in claim 1, wherein the frangible membrane comprises one or more pre-formed lines of weakness.

7. A dispensing device as claimed in claim 6, wherein the one or more pre-formed lines of weakness form a star pattern.

8. A dispensing device as claimed in claim 6, wherein the one or more pre-formed lines of weakness form a half-moon pattern.

9. A dispensing device as claimed in claim 1, wherein the powdered product is located on a porous membrane that is provided in the chamber.

10. A dispensing device as claimed in claim 9, wherein the porous membrane is made of porous paper or sintered plastic.

11. A dispensing device as claimed in claim 9, wherein the porous membrane has a pore size which is large enough to allow air through but not large enough to allow the powdered product through.

12. A dispensing device as claimed in claim 11, wherein the porous membrane is made of porous paper or sintered plastic.

13. A dispensing device as claimed in claim 1, wherein the housing further comprises a finger rest.

14. A dispensing device as claimed in claim 1, wherein the plunger comprises a thumb rest.

15. A dispensing device as claimed in claim 1, wherein the plunger is prevented from being removed from the housing by co-operating means.

16. A dispensing device as claimed in claim 15, wherein the co-operating means comprises at least one lug provided on an inner wall of the housing which cooperates with a channel provided on an outer wall of the plunger.

17. A dispensing device as claimed in claim 1, wherein the housing is provided with an inwardly directed shoulder against which, in use, the sheathing member abuts.

18. A dispensing device as claimed in claim 17, wherein the sheathing member comprises an outwardly directed shoulder which, in use, abuts the inwardly directed shoulder of the housing.

19. A dispensing device as claimed in claim 1, wherein the inlet of the sheathing member is radially directed and the chamber comprises a radially directed aperture.

20. A dispensing device as claimed in claim 19, wherein the inlet of the sheathing member and the chamber aperture are movable into alignment when the dispensing device is actuated.

21. A dispensing device as claimed in claim 19, wherein the radially directed aperture is located at an end of the chamber remote from the first outlet.

22. A dispensing device as claimed in claim 1, wherein at least the housing is a moulded component.

23. A dispensing device as claimed in claim 1, wherein the plunger is a moulded component.

24. A dispensing device as claimed in claim 1, wherein the sheathing member is a moulded component.

25. A dispensing device as claimed in claim 1, formed from one or more of polyethylene, polypropylene, polyester or a thermoplastic elastomer.

26. A dispensing device as claimed in claim 1, wherein the first outlet is adapted for nasal delivery of powdered products.

27. A dispensing device as claimed in claim 1, wherein the first outlet is adapted for oral delivery of powdered products.

* * * * *